United States Patent
True et al.

(10) Patent No.: US 9,283,379 B2
(45) Date of Patent: Mar. 15, 2016

(54) PINCH TO OPEN CUFF ELECTRODE

(71) Applicant: Cardiac Pacemakers, Inc., St. Paul, MN (US)

(72) Inventors: Kyle True, Minneapolis, MN (US); Brian Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/041,020

(22) Filed: Sep. 30, 2013

(65) Prior Publication Data

US 2014/0094887 A1    Apr. 3, 2014

Related U.S. Application Data

(60) Provisional application No. 61/709,146, filed on Oct. 2, 2012.

(51) Int. Cl.
*A61N 1/05* (2006.01)

(52) U.S. Cl.
CPC .................................. *A61N 1/0556* (2013.01)

(58) Field of Classification Search
None
See application file for complete search history.

(56) References Cited

U.S. PATENT DOCUMENTS

| | | | |
|---|---|---|---|
| 4,177,818 A | 12/1979 | De Pedro | |
| 4,573,481 A | 3/1986 | Bullara | |
| 4,590,946 A | 5/1986 | Loeb | |
| 4,590,949 A | 5/1986 | Pohndorf | |
| 4,602,624 A | 7/1986 | Naples et al. | |
| 4,628,942 A | 12/1986 | Sweeney et al. | |
| 4,740,170 A | 4/1988 | Lee et al. | |
| 4,920,979 A | 5/1990 | Bullara | |
| 4,940,065 A | 7/1990 | Tanagho et al. | |
| 4,979,511 A | 12/1990 | Terry, Jr. | |
| 5,031,621 A | 7/1991 | Grandjean et al. | |
| 5,095,905 A | 3/1992 | Klepinski | |
| 5,215,089 A | 6/1993 | Baker et al. | |
| 5,218,089 A | 6/1993 | Mariotti et al. | |
| 5,251,634 A | 10/1993 | Weinberg | |
| 5,259,394 A | 11/1993 | Bens | |

(Continued)

FOREIGN PATENT DOCUMENTS

AU    2012275666 B2    6/2015
EP    0585553 A1    6/1993

(Continued)

OTHER PUBLICATIONS

International Search Report and Written Opinion issued in PCT/US2014/015590, mailed May 28, 2014, 14 pages.

(Continued)

*Primary Examiner* — Erica Lee
(74) *Attorney, Agent, or Firm* — Faegre Baker Daniels LLP

(57) ABSTRACT

The present invention provides a cuff electrode assembly for implantation on a target nerve. The cuff electrode assembly can include a resilient cuff body configured to be disposed about the target nerve. The cuff body includes a first end portion having a first free end, and a second end portion having a second free end. The cuff electrode assembly further includes a first arm member and a second arm member each projecting radially outward from the cuff body and spaced from one another along the cuff body. The cuff body can be configured such that a force applied to urge the first and second arm members toward one another defines an open configuration of the cuff body configured to allow the cuff body to be positioned around the target nerve. The cuff electrode assembly further includes an electrode oriented to provide electrical stimuli to the target nerve.

20 Claims, 9 Drawing Sheets

(56) References Cited

U.S. PATENT DOCUMENTS

| | | | |
|---|---|---|---|
| 5,282,468 A | 2/1994 | Klepinski |
| 5,324,322 A | 6/1994 | Grill, Jr. et al. |
| 5,334,438 A | 8/1994 | Saugnac |
| 5,344,438 A | 9/1994 | Testerman et al. |
| 5,351,394 A | 10/1994 | Weinberg |
| 5,358,516 A | 10/1994 | Myers et al. |
| 5,375,594 A | 12/1994 | Cueva |
| 5,505,201 A | 4/1996 | Grill et al. |
| 5,531,778 A | 7/1996 | Maschino et al. |
| 5,674,272 A | 10/1997 | Bush et al. |
| 5,689,877 A | 11/1997 | Grill et al. |
| 5,755,766 A | 5/1998 | Chastain et al. |
| 5,782,892 A | 7/1998 | Castle et al. |
| 5,871,530 A | 2/1999 | Williams et al. |
| 5,913,876 A | 6/1999 | Taylor et al. |
| 5,964,702 A | 10/1999 | Grill et al. |
| 6,038,479 A | 3/2000 | Werner et al. |
| 6,051,017 A | 4/2000 | Loeb et al. |
| 6,093,197 A | 7/2000 | Bakula et al. |
| 6,174,329 B1 | 1/2001 | Callol et al. |
| 6,178,349 B1 | 1/2001 | Kieval |
| 6,249,708 B1 | 6/2001 | Nelson et al. |
| 6,292,703 B1 | 9/2001 | Meier et al. |
| 6,296,659 B1 | 10/2001 | Foerster |
| 6,308,104 B1 | 10/2001 | Taylor et al. |
| 6,308,105 B1 | 10/2001 | Duysens et al. |
| 6,381,499 B1 | 4/2002 | Taylor et al. |
| 6,423,080 B1 | 7/2002 | Gellman et al. |
| 6,600,956 B2 | 7/2003 | Maschino et al. |
| 6,725,096 B2 | 4/2004 | Chinn et al. |
| 7,047,081 B2 | 5/2006 | Kuzma |
| 7,054,692 B1 | 5/2006 | Whitehurst et al. |
| 7,160,298 B2 | 1/2007 | Lawew et al. |
| 7,212,867 B2 | 5/2007 | Van Venrooij et al. |
| 7,502,650 B2 | 3/2009 | Kieval |
| 7,536,227 B1 | 5/2009 | Poore et al. |
| 7,561,923 B2 | 7/2009 | Libbus et al. |
| 7,711,421 B2 | 5/2010 | Shafer et al. |
| 7,749,273 B2 | 7/2010 | Cauthen, III et al. |
| 7,807,925 B2 | 10/2010 | Zarembo |
| 7,831,311 B2 | 11/2010 | Cross, Jr. et al. |
| 7,891,085 B1 | 2/2011 | Kuzma et al. |
| 7,925,352 B2 | 4/2011 | Stack et al. |
| 7,925,358 B2 | 4/2011 | Beiden et al. |
| 7,933,662 B2 | 4/2011 | Marshall et al. |
| 7,957,817 B1 | 6/2011 | Gillespie et al. |
| 7,974,706 B2 | 7/2011 | Moffitt et al. |
| 7,996,092 B2 * | 8/2011 | Mrva et al. ............. 607/118 |
| 8,100,141 B2 | 1/2012 | Slupecki et al. |
| 8,155,757 B1 | 4/2012 | Neisz et al. |
| 8,244,372 B1 | 8/2012 | Zhulati et al. |
| 8,295,948 B2 | 10/2012 | Barker et al. |
| 8,326,418 B2 | 12/2012 | Sommer et al. |
| 8,417,343 B2 | 4/2013 | Bolea et al. |
| 8,452,406 B2 | 5/2013 | Arcot-Krishnamurthy et al. |
| 8,483,845 B2 | 7/2013 | Sage |
| 8,548,593 B2 | 10/2013 | Ternes et al. |
| 8,639,355 B2 | 1/2014 | Soltis |
| 2002/0116042 A1 | 8/2002 | Boling |
| 2002/0128700 A1 | 9/2002 | Cross, Jr. |
| 2003/0040785 A1 | 2/2003 | Maschino et al. |
| 2003/0236558 A1 | 12/2003 | Whitehurst et al. |
| 2004/0010303 A1 | 1/2004 | Bolea et al. |
| 2004/0111139 A1 | 6/2004 | McCreery |
| 2005/0209655 A1 | 9/2005 | Bradley et al. |
| 2005/0234512 A1 | 10/2005 | Nakao |
| 2005/0283246 A1 | 12/2005 | Cauthen, III et al. |
| 2006/0030919 A1 | 2/2006 | Mrva et al. |
| 2006/0122675 A1 | 6/2006 | Libbus et al. |
| 2006/0190042 A1 | 8/2006 | Stone et al. |
| 2006/0259078 A1 | 11/2006 | Libbus |
| 2007/0071568 A1 | 3/2007 | Dorstewitz |
| 2007/0083236 A1 | 4/2007 | Sikora et al. |
| 2007/0100406 A1 | 5/2007 | Kollatschny et al. |
| 2007/0118177 A1 | 5/2007 | Libbus et al. |
| 2007/0142871 A1 | 6/2007 | Libbus et al. |
| 2007/0173914 A1 | 7/2007 | Kollatschny |
| 2007/0203556 A1 | 8/2007 | Rutten et al. |
| 2007/0239243 A1 | 10/2007 | Moffitt et al. |
| 2007/0255320 A1 | 11/2007 | Inman et al. |
| 2008/0046058 A1 | 2/2008 | Cross et al. |
| 2008/0051839 A1 | 2/2008 | Libbus et al. |
| 2008/0058871 A1 | 3/2008 | Libbus et al. |
| 2008/0058874 A1 | 3/2008 | Westlund et al. |
| 2008/0058901 A1 | 3/2008 | Ternes et al. |
| 2008/0086181 A1 | 4/2008 | Amurthur et al. |
| 2008/0091255 A1 | 4/2008 | Caparso et al. |
| 2008/0103407 A1 | 5/2008 | Bolea et al. |
| 2008/0103545 A1 | 5/2008 | Bolea et al. |
| 2008/0132987 A1 | 6/2008 | Westlund et al. |
| 2008/0140092 A1 | 6/2008 | Stone et al. |
| 2008/0172101 A1 | 7/2008 | Bolea et al. |
| 2008/0177365 A1 | 7/2008 | Bolea et al. |
| 2008/0177366 A1 | 7/2008 | Bolea et al. |
| 2008/0183258 A1 | 7/2008 | Inman |
| 2008/0195188 A1 | 8/2008 | Libbus et al. |
| 2008/0234780 A1 | 9/2008 | Smith et al. |
| 2008/0255613 A1 | 10/2008 | Kaiser et al. |
| 2009/0048641 A1 | 2/2009 | Libbus |
| 2009/0210042 A1 | 8/2009 | Kowalczewski |
| 2009/0259260 A1 | 10/2009 | Bentley et al. |
| 2009/0275997 A1 | 11/2009 | Faltys et al. |
| 2009/0276024 A1 | 11/2009 | Bonde et al. |
| 2009/0318961 A1 | 12/2009 | Stone et al. |
| 2010/0023088 A1 | 1/2010 | Stack et al. |
| 2010/0036451 A1 | 2/2010 | Hoffer |
| 2010/0121405 A1 | 5/2010 | Ternes et al. |
| 2010/0145221 A1 * | 6/2010 | Brunnett et al. ............. 600/554 |
| 2010/0168831 A1 | 7/2010 | Korivi et al. |
| 2010/0211131 A1 | 8/2010 | Williams et al. |
| 2010/0286553 A1 | 11/2010 | Feler et al. |
| 2010/0305674 A1 | 12/2010 | Zarembo et al. |
| 2010/0312320 A1 | 12/2010 | Faltys et al. |
| 2010/0331938 A1 | 12/2010 | Sommer et al. |
| 2011/0004281 A1 | 1/2011 | Jones |
| 2011/0022142 A1 | 1/2011 | Barker et al. |
| 2011/0040257 A1 | 2/2011 | Behymer et al. |
| 2011/0060395 A1 | 3/2011 | Cantlon |
| 2011/0172682 A1 | 7/2011 | Brady et al. |
| 2011/0172701 A1 | 7/2011 | Wales et al. |
| 2012/0022617 A1 | 1/2012 | Tockman et al. |
| 2012/0035691 A1 | 2/2012 | Tockman et al. |
| 2012/0065702 A1 | 3/2012 | Arcot-Krishnamurthy et al. |
| 2012/0158082 A1 * | 6/2012 | Katra ............................. 607/17 |
| 2012/0221087 A1 | 8/2012 | Parnis et al. |
| 2013/0005169 A1 | 1/2013 | Soltis et al. |
| 2013/0013045 A1 | 1/2013 | Soltis |
| 2013/0172973 A1 | 7/2013 | Tockman et al. |
| 2013/0253615 A1 | 9/2013 | Arcot-Krishnamurthy et al. |
| 2013/0253624 A1 | 9/2013 | Tockman et al. |
| 2014/0094888 A1 | 4/2014 | True et al. |

FOREIGN PATENT DOCUMENTS

| | | |
|---|---|---|
| JP | 2005058456 A | 3/2005 |
| JP | 2008526299 A | 7/2008 |
| JP | 2015511857 A | 4/2015 |
| WO | WO9929366 A1 | 6/1999 |
| WO | WO2004052176 A2 | 6/2004 |
| WO | WO2006093685 A1 | 9/2006 |
| WO | WO2007024164 A1 | 1/2007 |
| WO | WO2008088798 A1 | 7/2008 |
| WO | WO2008094349 A1 | 8/2008 |
| WO | WO2009020639 A1 | 2/2009 |
| WO | WO2009025817 A2 | 2/2009 |
| WO | WO2009100242 A2 | 8/2009 |
| WO | WO2011053766 A1 | 5/2011 |
| WO | 2013142053 A1 | 9/2013 |

OTHER PUBLICATIONS

International Search Report and Written Opinion Issued in PCT/US2009/063442, mailed Feb. 1, 2010, 11 pages.

(56) References Cited

OTHER PUBLICATIONS

International Search Report and Written Opinion Issued in PCT/US2010/026350, mailed Jun. 2, 2010.
International Search Report and Written Opinion Issued in PCT/US2011/049585, mailed Dec. 19, 2011.
International Search Report and Written Opinion Issued in PCT/US2012/044020, mailed Sep. 11, 2012, 9 pages.
International Search Report and Written Opinion issued in PCT/US2012/044028, mailed Oct. 1, 2012, 9 pages.
International Search Report and Written Opinion issued in PCT/US2012/071812, mailed Sep. 13, 2013, 12 pages.
International Search Report and Written Opinion issued in PCT/US2013/029306, mailed Jul. 18, 2013, 13 pages.
International Search Report and Written Opinion issued in PCT/US2013/077949, mailed Jun. 20, 2014, 15 pages.
Kirsch, Robert F. et al., "Restoration of Hand and Arm Function by Functional Neuromuscular Stimulation", Period covered: Jun. 1, 2001-Aug. 31, 2006, 71 pages.
International Search Report and Written Opinion issued in PCT/US2011/020699, mailed Jul. 26, 2011, 24 pages.
International Search Report and Written Opinion issued in PCT/US2013/062560, mailed Dec. 17, 2014, 13 pages.
International Search Report and Written Opinion issued in PCT/US2013/062608, mailed Dec. 17, 2014, 13 pages.
Partial International Search Report issued in PCT/US2011/020699, mailed Mar. 24, 2011, 6 pages.
International Preliminary Examination Report, Chapter II, issued in PCT/US2013/029306, completed Aug. 19, 2014, 16 pages.
Written Opinion of the International Preliminary Examining Authority issued in PCT/US2013/029306, mailed May 8, 2014, 6 pages.
International Preliminary Report on Patentability issued in PCT/US2013/062560, completed Apr. 7, 2015, 9 pages.
International Preliminary Report on Patentability issued in PCT/US2013/062608, completed Apr. 7, 2015, 8 pages.
International Preliminary Report on Patentability issued in PCT/US2014/015590, mailed Aug. 27, 2015, 10 pages.

\* cited by examiner

PINCH TO OPEN CUFF ELECTRODE

CROSS-REFERENCE TO RELATED APPLICATION

This application claims the benefit of U.S. Provisional Application No. 61/709,146, filed Oct. 2, 2012, which is incorporated herein by reference in its entirety.

TECHNICAL FIELD

The present disclosure relates to implantable medical devices and method of implantation of such devices. More specifically, the disclosure relates to cuff electrode assemblies for implantation around a nerve.

BACKGROUND

Various types of electrodes can be used for providing electrical stimuli to a target location inside the body. One of them is a cuff shaped electrode, shaped as per the geometry of a typical nerve or nerve fiber having a generally annular shape. Cuff shaped electrodes are designed to provide stimulation or record an electro-gram from tissues/peripheral nerves. The cuff shaped electrodes can generally include a dielectric material and defines a lumen having a sufficient diameter to receive a nerve that needs to be electrically stimulated. There exists a continuing need for improved cuff electrode assemblies.

SUMMARY

In Example 1, a cuff electrode assembly for implantation on a target nerve. The cuff electrode assembly comprises a resilient cuff body, first and second arm members, and an electrode. The cuff body is configured to be disposed about the target nerve, and includes a first end portion having a first free end, and a second end portion having a second free end, wherein the cuff body is pre-formed to assume a closed configuration having a generally annular cross-sectional shape. The first and second arm members each project radially outward from the cuff body and are spaced from one another along the cuff body, wherein each of the first and second arm members is disposed closer along the cuff body to the first free end than to the second free end. The cuff body is configured such that a force applied to urge the first and second arm members toward one another causes relative deflection of the second free end and the first free end away from one another to define an open configuration of the cuff body configured to allow the cuff body to be positioned around the target nerve. The electrode is disposed at least partially within or on the cuff body and is oriented to provide an electrical stimuli to the target nerve when the cuff body is disposed about the target nerve.

In Example 2, the cuff electrode assembly of Example 1, wherein a length of the cuff extending from the first free end to the second free end spans an angle less than 360 degrees.

In Example 3, the cuff electrode assembly of Example 1, wherein in the closed configuration the second end portion of the cuff body overlaps the first end portion of the cuff body.

In Example 4, the cuff electrode assembly of any of Examples 1-3, wherein the cuff body is pre-formed such that in the closed configuration the first free end and the second free end are spaced apart from one another without overlap so such that the cuff body further defines a generally circular cross-sectional.

In Example 5, the cuff electrode assembly of any of Examples 1-4, wherein the first arm member is positioned closer than the second arm member to the first free end, and wherein the second arm member is positioned along the cuff body between the first arm member and the second free end.

In Example 6, the cuff electrode assembly of any of Examples 1-5, wherein the cuff body is configured such that the first arm member remains relatively stationary and the second arm member deflects toward the first arm member upon application of a force to the second arm member in the direction of the first arm member so as to cause the cuff body to assume the open configuration.

In Example 7, the cuff electrode assembly of any of Examples 1-6, wherein the cuff body is configured such that a length of the first end portion between the first arm member and the first free end remains relatively stationary upon application of a force to the second arm member urging the second arm member toward the first arm member.

In Example 8, the cuff electrode assembly of any of Examples 1-7, wherein the cuff body is made substantially of a flexible, electrically insulating polymer.

In Example 9, the cuff electrode assembly of any of Examples 1-8, wherein the flexible insulating polymer is silicone rubber.

In Example 10, the cuff electrode assembly of any of Examples 1-9, wherein the cuff body further includes a reinforcing material in the flexible, electrically insulating polymer.

In Example 11, the cuff electrode assembly of any of Examples 1-10, wherein the cuff body further includes a stiffening member within the flexible, insulating polymer.

In Example 12, the cuff electrode assembly of any of Examples 1-10, further comprising a stiffening member configured to urge the cuff body to return to the pre-formed shape upon release of a force causing the cuff body to assume the open configuration.

In Example 13, the cuff electrode assembly of either of Examples 11 or 12, wherein the stiffening member is embedded within the flexible insulating polymer and has a first end portion and an opposite second end portion, the first end portion disposed proximate the second arm member, and the second end portion disposed proximate the second free end of the cuff body.

In Example 14, a lead assembly for stimulating a target nerve, the lead assembly comprising at least one cuff electrode assembly, a lead body, a conductor, and a connector assembly. The cuff electrode assembly is configured for implantation about the target nerve and comprises a resilient cuff body, a first arm member and a second arm member, and an electrode. The resilient cuff body is configured to be disposed about the target nerve, and includes a first end portion having a first free end, and a second end portion having a second free end, wherein the cuff body is pre-formed to define a generally annular cross-sectional shape. The arm members each project radially outward from the cuff body and are spaced from one another along the cuff body, wherein each of the first and second arm members is disposed closer along the cuff body to the first free end than to the second free end. The cuff body is configured such that a force applied to urge the first and second arm members toward one another causes relative deflection of the second free end and the first free end away from one another to define an open configuration of the cuff body configured to allow the cuff body to be positioned around the target nerve. The electrode is disposed at least partially within or on the cuff body and is oriented to provide an electrical stimuli to the target nerve when the cuff body is disposed about the target nerve. The lead body is flexible and is made of an insulating material, and further has proximal end portion and a distal end portion. The conductor member is flexible and insulated and is at least partially disposed within the lead body. The conductor member includes a distal end electrically and mechanically coupled to the electrode of the cuff electrode assembly. The connector assembly is coupled to the proximal end portion of the lead body and to the conductor member, and is configured to electrically couple the conductor member to an implantable stimulator.

In Example 15, the lead assembly of Example 14, wherein the at least one cuff electrode assembly includes a plurality of cuff electrode assemblies, and wherein the lead further includes a plurality of insulated, flexible conductor members at least partially disposed within the lead body, and wherein an electrode of each of the plurality of cuff electrode assemblies is electrically and mechanically coupled to one of the plurality of conductor members.

In Example 16, the lead assembly of Example 14, wherein the cuff electrode assembly further comprises a stiffening member configured to urge the cuff body to return to the pre-formed shape upon release of a force causing the cuff body to assume the open configuration.

In Example 17, the lead assembly of any of Examples 14-16, wherein in the closed configuration the second end portion of the cuff body overlaps the first end portion of the cuff body.

In Example 18, a method for implanting a cuff electrode assembly on a target nerve. The method comprises inserting an implantable cuff electrode assembly within a patient's body. The cuff electrode assembly includes a resilient cuff body configured to be disposed about the target nerve, first and second arm members, and an electrode. The cuff body includes a first end portion having a first free end, and a second end portion having a second free end, wherein the cuff body is pre-formed to assume a closed configuration having a generally annular cross-sectional shape. The first arm member and the second arm member each project radially outward from the cuff body and are spaced from one another along the cuff body, wherein each of the first and second arm members is disposed closer along the cuff body to the first free end than to the second free end, and further wherein the cuff body is configured such that a force applied to urge the first and second arm members toward one another causes relative deflection of the second free end and the first free end away from one another to define an open configuration of the cuff body configured to allow the cuff body to be positioned around the target nerve. The electrode is disposed at least partially within or on the cuff body and is oriented to provide an electrical stimuli to the target nerve when the cuff body is disposed about the target nerve. The method further comprises applying a force to at least one of the first and second arm members to urge the first and second arm members toward one another thereby causing the first and second free ends to deflect away from one another such that the cuff body assumes the open configuration. Next, with the cuff body in the open configuration, the method comprises placing the cuff electrode assembly proximate the target nerve such that the cuff body at least partially surrounds the target nerve, and then releasing the force urging the first and second arm members together.

In Example 19, the method of Example 18, wherein the cuff electrode assembly is a first cuff electrode assembly of an implantable lead assembly including one or more additional cuff electrode assemblies, the one or more additional cuff electrode assemblies being coupled to the first cuff electrode assembly.

In Example 20, the method of Example 19, wherein the method further comprises simultaneously opening the first cuff electrode assembly and the one or more additional cuff electrode assemblies.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
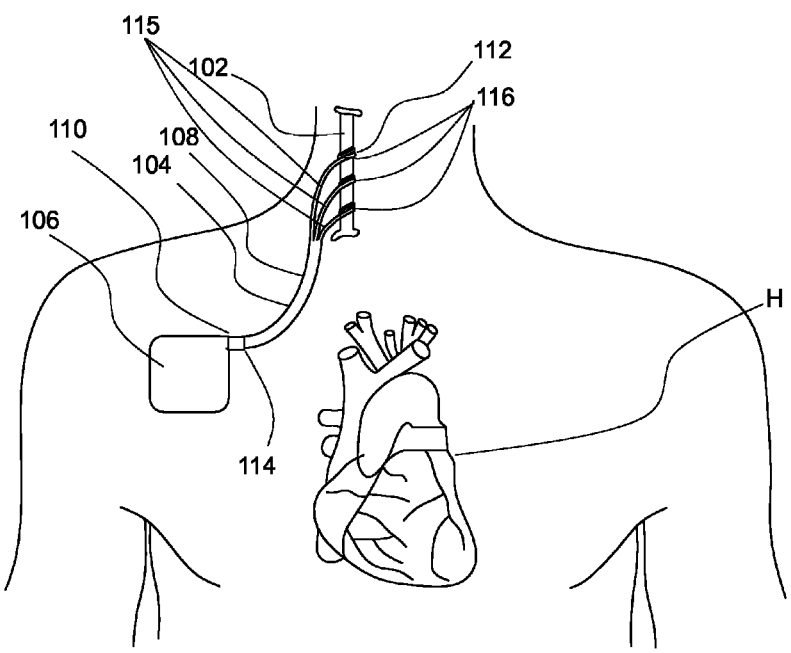
FIG. 1 is a schematic illustration of a system in an implanted state, according to an embodiment of the present invention.

While the invention is amenable to various modifications and alternative forms, specific embodiments have been shown by way of example in the drawings and are described in detail below. However, the intention is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an implantable system 100 for stimulating a target nerve 102. As shown, the system 100 includes an implantable lead assembly 104 coupled to an implantable medical device (IMD) 106. In the illustrated embodiment, the lead assembly 104 includes a lead body 108 having a proximal end portion 110 and a distal end portion 112, a connector assembly 114, a plurality of insulated conductor members 115, and a plurality of cuff electrode assemblies 116. In various embodiments, each of the conductor members 115 can be partially disposed within the lead body 108 and extend distally from the distal end portion 112 thereof. As further shown, each of the cuff electrode assemblies 116 is coupled to one of the conductor members 115. In addition, in the illustrated embodiment, the connector assembly 114 is coupled to and extends from the proximal end portion 110 of the lead body 108. The connector assembly 114 is operable to mechanically couple the lead assembly 104 to the IMD 106, and also to electrically couple each of the conductor members 115 to electronics within the IMD 106. In various embodiments, the connector assembly 114 can be a multipolar connector, with a plurality of electrical contacts (not shown) each electrically connected to one of the conductor members 115, respectively.

During operation, the lead assembly 104 delivers electrical signals between the IMD 106 and the cuff electrode assemblies 116, which are configured to wrap around and thereby be secured to the target nerve 102. In various embodiments, the cuff electrode assemblies 116 can be separately controlled by IMD 106, such that the energy having different magnitude, phase, and/or timing characteristics may be delivered to or from each of the cuff electrode assemblies 116. While the lead assembly 104 shown includes three cuff electrode assemblies 116, more or fewer cuff electrode assemblies 116 can alternatively be employed in the system 100. In addition, one or more cuff electrode assemblies 116 may be alternatively configured as a strain relief cuff that does not carry electrical signals, but secures the lead assembly 104 relative to the nerve 104 to minimize movement of the active cuff electrode assemblies 116 relative to the excitable tissue due to voluntary or involuntary movements of the patient. Furthermore, the IMD 106 shown is merely by way of illustration. In various embodiments, the IMD 106 may have other configurations suitable for use in conjunction with the lead assembly and may be implanted in a suitable location in the patient's body. The IMD 106 can be implanted subcutaneously within the body, typically at a location such as in a patient's chest or abdomen, although other implantation locations are possible.

In various embodiments, the system 100 can be configured to sense and stimulate the sympathetic and/or parasympathetic nervous systems. Stimulating the sympathetic and parasympathetic nervous systems can have effects on physiological parameters associated with the heart H, such as heart rate and blood pressure. In addition, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

In one embodiment, the target nerve 102 is the vagus nerve and specifically, the right vagus nerve. In such embodiments, the cuff electrode assemblies 116 can be arranged around the vagus nerve, with the IMD 106 configured to deliver energy to the cuff electrode assemblies 116 to stimulate the vagus nerve. The vagus nerve has afferent properties such that the neural stimulation is transmitted to the central nervous system (CNS). Vagal stimulation simultaneously increases parasympathetic and decreases sympathetic activity, and is believed to prevent further remodeling or predisposition to fatal arrhythmias in post-MI patients to help restore autonomic balance and increase heart rate variability (HRV), increase parasympathetic and reduce sympathetic tone in hypertrophic cardiac myopathy (HCM), neurogenic hypertension, and arrhythmia protection, reduce anginal symptoms, increase coronary blood flow (CBF), and to prevent development or worsening of congestive heart failure (CHF) following MI. The cuff electrode assemblies 116 can be configured and arranged to stimulate the vagus nerve N to provide the physiological responses described. While the cuff electrode assemblies 116 are shown arranged around the right vagus nerve in FIG. 1, the cuff electrode assemblies 116 can be configured and arranged to stimulate the left vagus nerve to treat other physiological and psychological conditions such as epilepsy and depression.

Figure 2:
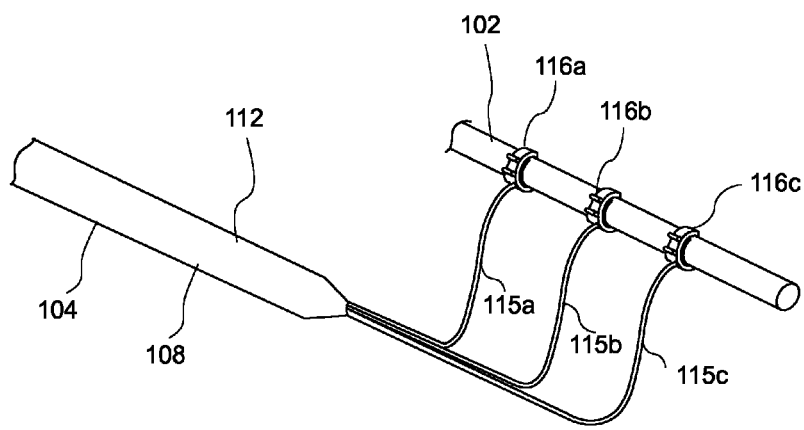
FIG. 2 is a schematic illustration of a lead assembly included in the system of FIG. 1, according to an embodiment of the present invention.

FIG. 2 is a schematic perspective view of a portion of the implantable lead assembly 104 showing the cuff electrode assemblies 116 wrapped about the target nerve 102. In the particular embodiment shown in FIG. 2, the plurality of cuff electrode assemblies 116 of the lead assembly 104 includes three cuff electrode assemblies 116a, 116b, 116c, and also three conductor members 115a, 115b, 115c, each extending distally with respect to the lead body distal end portion 112 and coupled to a corresponding one of the cuff electrode assemblies 116a, 116b, 116c. As discussed previously, however, in other embodiments, more or fewer cuff electrode assemblies 116 and the conductor members can be utilized in a given lead assembly 104.

As will be explained in greater detail herein, the cuff electrode assemblies 116a, 116b, 116c are each configured to be manipulated during implantation so that they can be disposed over the target nerve 102 and wrap at least partially about the target nerve 102 while applying sufficient radial and frictional forces against the target nerve 102 so as to retain themselves in the implantation position selected by the clinician. Additionally, each cuff electrode assemblies 116a, 116b, 116c includes an electrode (not shown in FIG. 1 or 2) oriented toward the target nerve 102 to provide the selected therapeutic stimuli thereto.

In various embodiments, each of the insulated conductor members 115a, 115b, 115c includes an inner conductor element (not shown) covered by an outer insulating layer that operates to electrically isolate the inner conductor element from the outside environment. Each of the conductor elements is electrically coupled to the electrode of one of the cuff electrode assemblies 116a, 116b, 116c.

In various embodiments, the lead body 108 can be formed of an electrically insulative material and can also be operable to electrically isolate the various conductor members 115a, 115b, 115c from the external environment, as well as to provide structural support for the lead assembly 104 as a whole. In various embodiments, the insulating layers of the conductor members 115a, 115b, 115c can be integrally formed with the lead body 108. Alternatively, the lead body 108 can initially be a separate, tubular element and the insulated conductor members 115a, 115b, 115c can thereafter be strung through the lead body 108. The conductor elements of the conductor members 115a, 115b, 115c can be of a configuration providing the requisite electrical and mechanical properties for a particular lead assembly 104. In various embodiments, such conductor elements can be single or multi-filar conductor coils. In various embodiments, the conductor elements can be single or multi-strand cable conductors.

Exemplary materials for use in the lead body 108 and the conductor member electrical insulating layers include, without limitation, polymeric materials such as styrene isoprene butadiene (SIBS), polytetrafluoroethylene (PTFE), polyethylene (PE), polypropylene (PP), fluorinated ethylene propylene (FEP), ethylene-tetrafluoroethylene (ETFE), or another biocompatible polymer. Exemplary materials for the conductor elements can include, without limitation, MPTa, Pt-clad Ta, Pt-clad MP35N, MP35N, low-titanium MP35N, MPAg, and Nitinol. However, it is emphasized that the foregoing insulator and conductor materials are included for illustration purposes only and are in no way intended to be exhaustive listings of the suitable materials that can be utilized.

Figure 3A:
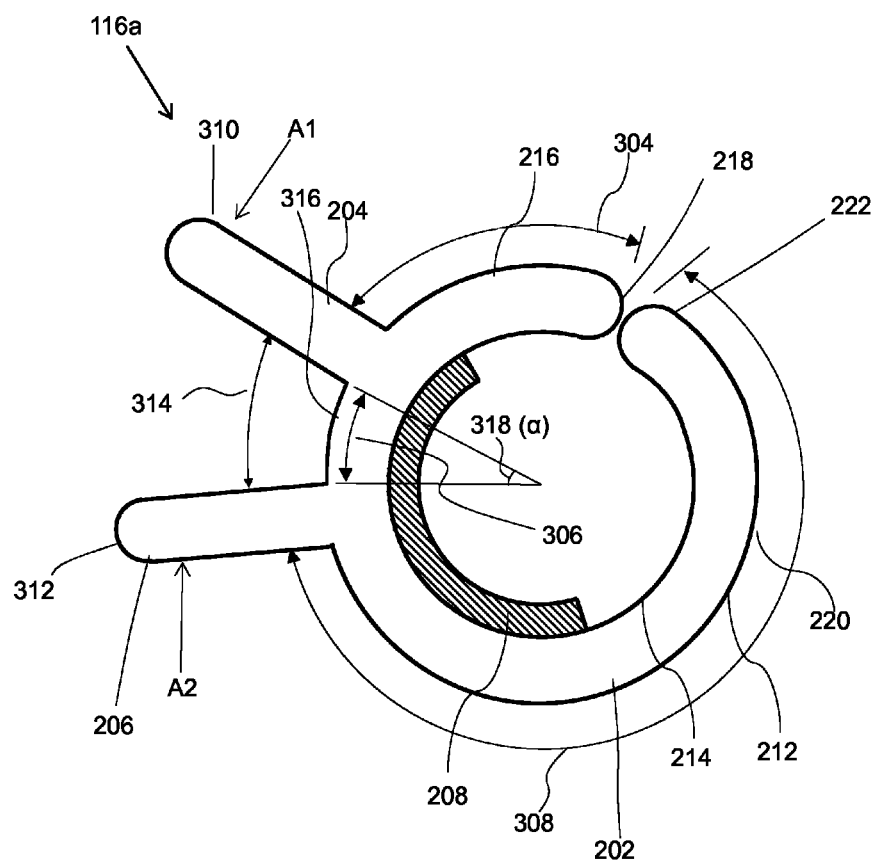
FIG. 3A is a schematic front view of a cuff electrode assembly included in the system of FIG. 1 in a closed configuration that can be used in relation to embodiments of the present invention.
Figure 3B:
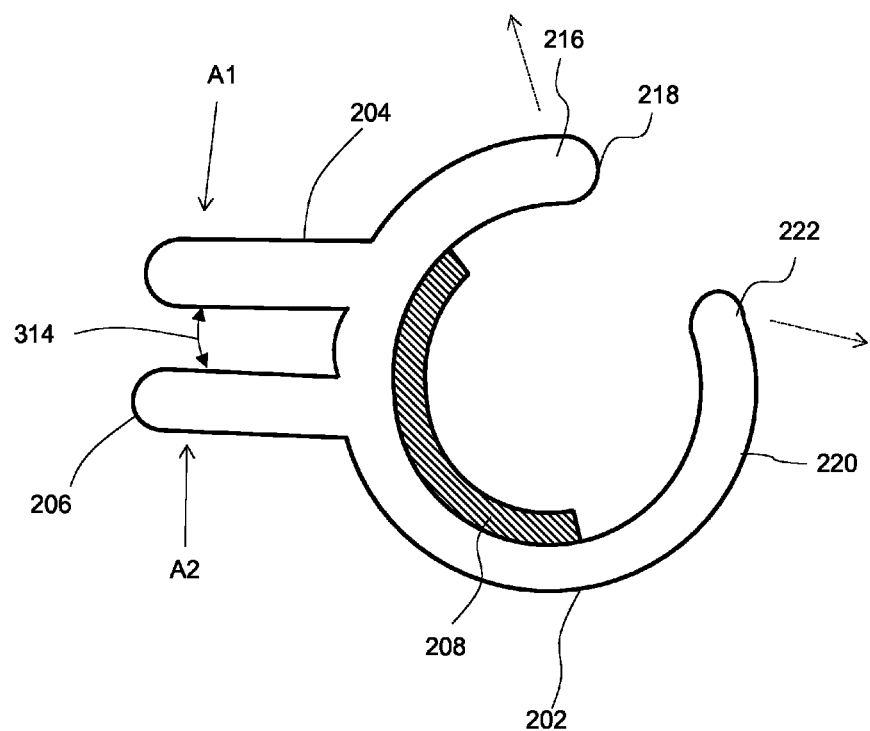
FIG. 3B is a schematic front view of the cuff electrode assembly of FIG. 3A in an open configuration that can be used in relation to embodiments of the present invention.

FIG. 3A is a schematic front view of the cuff electrode assembly 116a in a closed configuration (i.e., the configuration assumed in its implanted state around a target nerve 102). FIG. 3B is a front view of the cuff electrode assembly 116a in an open configuration (i.e., the configuration assumed so as to allow the clinician to place the cuff electrode assembly 116a around the target nerve 102). It will be appreciated that the cuff electrode assemblies 116b, 116c can be configured in substantially the same or an identical manner as the cuff electrode assembly 116a.

As shown, the cuff electrode assembly 116a includes a resilient cuff body 202, a pair of arm members 204, 206, and an electrode 208. In addition, the cuff body 202 includes an outer surface 212, an inner surface 214, a first end portion 216 having a first free end 218, and a second end portion 220 having a second free end 222. The cuff body 202 has a length extending between the first and second free ends 218 and 222. As further shown, the arm members 204 and 206 each project radially outward from the cuff body 202, and are spaced from one another along the cuff body 202. In the illustrated embodiment, the first arm member 204 is positioned closer than the second arm member 206 to the first free end 218, and the second arm member 206 is positioned closer to the first free end 218 than to the second free end 222. In various other embodiments, the specific placement of the first arm member 204 and the second arm member 206 can be varied from that shown. For example, in one embodiment, the second arm member 206 can be positioned generally equidistant from the first free end 218 and the second free end 222, with the first arm member 204 positioned between the second arm member 206 and the first free end 218.

Thus, as shown in FIG. 3A, the cuff body 202 has a length including a first portion length 304, a middle portion length 306, and a second portion length 308. The first portion length 304 can extend along the cuff body 202 from the first free end 218 to the first arm member 204. The middle portion length 306 can extend along the cuff body 202 from the first arm member 204 to that second arm member 206. The second portion length 308 can extend along the cuff body 202 from the second arm member 206 to the second free end 222. In an embodiment, the second portion length 308 can be greater than the first portion length 304 so as to enable each of the first arm member 204 and the second arm member 206 to be disposed closer along the cuff body 202 to the first free end 218 than to the second free end 222.

As further shown, the cuff body 202 can assume, in its closed configuration, a generally annular cross-sectional shape. In various embodiments, the cuff body 202 is preformed to tend to assume the closed configuration shown in FIG. 3A in the absence of an external force urging all or a portion of the cuff body 202 to assume the open configuration (e.g., as shown in FIG. 3B). In various embodiments, the cuff body 202 is configured so that the length of the cuff body 202 spans an angle less than 360 degrees in the closed configuration. As shown, in the closed configuration, the first free end 218 and the second free end 222 are spaced apart from one another without overlap such that the cuff body 202 defines a generally annular cross-sectional shape when viewed in the front end view of FIG. 3A. In the illustrated embodiment, the annular cross-sectional shape is generally circular.

In various embodiments, the cuff body 202 can be formed of a polymeric material that provides sufficient resiliency to allow the cuff body 202 to be deflected toward the open configuration and thereafter return to the pre-formed, closed configuration. In one embodiment, the cuff body 202 can be made substantially of a flexible, electrically insulating polymer. In one embodiment, the cuff body 202 can be made from a silicone rubber. In some embodiments, the cuff body 202 can include additional structure, e.g., additives or reinforcing elements incorporated or embedded into the polymeric material to enhance the mechanical strength and/or resiliency of the cuff body 202.

The cuff body 202 can be configured such that a force applied to urge the first and second arm members 204 and 206 toward one another can cause relative deflection of the second free end 222 and the first free end 218 away from one another to define the open configuration of the cuff body as shown in FIG. 3B. The open configuration allows the cuff body 202 to be positioned around the target nerve 102. Upon subsequent removal of the aforementioned force, the cuff body 202 can then attempt to resume its closed configuration, thus applying a radial force on the target nerve 102 to secure the cuff electrode assembly 116a in place as illustrated in FIGS. 1 and 2.

In the illustrated embodiment, the first arm member 204 has a distal portion 310 and the second arm member 206 has a distal portion 312. In use, a force can be applied to the distal portion 310 of the first arm member 204 and the distal portion 312 of the second arm member 206 so as to achieve the open configuration. For example, the force can be applied on the first arm member 204 such as along a direction A1 and on the second arm member 206 such as along a direction A2. In an embodiment, the distal portion 310 of the first arm member 204 and the distal portion 312 of the second arm member 206 can be separated by an arm member distance 314 such as shown in FIG. 3A, while the assembly is in the completely closed state without any force applied thereon. The arm member distance 314 can be subject to a change in dimension depending upon the magnitude of the force applied on the arm members 204 and 206. The force can be applied to urge the first arm member 204 and the second arm member 206 toward one another so as to reduce the arm member distance 314. This, in turn, results in deflection of the first and second free ends 218 and 222 from their positions, when in the closed configuration. In some embodiments, the cuff body 202 is configured such that the second arm member 206 remains almost stationary and the first arm member 204 deflects toward the second arm member 206 upon application of force to the first arm member 204 in the direction A1 so as to cause the cuff body 202 to assume the open configuration.

In various embodiments, the cuff body 202 can be configured such that the first arm member 204 can be held by the clinician relatively stationary while a force is applied to the second arm member 206 in the direction of the first arm member 204. In such embodiments, the force causes the second arm member 206 to deflect toward the first arm member 204 so as to cause the cuff body 202 to assume the open configuration. Additionally, in various embodiments, the cuff body 202 can be configured such that the first length portion 304 remains relatively stationary upon application of a force to the second arm member 206 urging the second arm member 206 toward the first arm member 204.

In an embodiment, the first arm member 204 and the second arm member 206 and a portion of the cuff body 202 proximate to the first arm member 204 and the second arm member 206 define a pinch hinge portion 316 of the cuff electrode assembly 116a. In an embodiment, the pinch hinge portion 316 can be defined by a portion separated by the arm member distance 314 and includes the middle portion length 306 and the arm members 204 and 206. The pinch hinge portion 316 can be configured to allow the first arm member 204 and the second arm member 206 to form a hinge angle 318 (α) such that the hinge angle 318 (α) can be less than 180 degrees while the cuff body 202 assumes a completely closed configuration without any force applied thereon.

In addition, as shown, the electrode 208 is positioned on the inner surface 214 of the cuff body 202 such that it can be oriented toward and/or against the target nerve 102 (see FIGS. 1 and 2) to provide electrical stimuli to the target nerve 102 when the cuff electrode assembly 116a is placed thereupon. In various embodiments, the electrode 208 can be disposed at least partially within or on the cuff body 202. In an embodiment, the electrode 208 can be disposed at any portion of the length of the cuff body 202 for stimulating and/or sensing the target nerve 102 such as the vagus nerve. Exemplary materials used for the electrode 208 can include, without limitation, platinum, titanium, iridium, and alloys of any of the foregoing.

In the various embodiments, the design of the cuff electrode assembly 116a is simple and easy to operate such that a physician/user does not need any specific training to close or open or to modify the cuff electrode assembly 116a. In an example, the cuff electrode assembly 116a can be configured to be actuated directly by manipulating the cuff body 202 and the first and second arm members 204 and 206. In an example, the cuff electrode assembly 116a can be configured to be actuated by an implant tool (not shown). In various embodiments, for example, an implant tool can be configured to simultaneously apply force to all arm members of all cuff assemblies 116 on a given lead assembly 104 so that all such cuff electrode assemblies 116 can be deployed on a target nerve 102 simultaneously. In addition, the particular configuration of the arm members 204, 206 relative to the first and second free ends 218, 222 (i.e., with the arm members 204, 206 being closer to the first free end 218 than to the second free end 222) can provide the additional advantage in that it can minimize the length of the cuff body 202 that the clinician must wrap around the circumferential portion of the target nerve opposite the portion to which the clinician has direct visual access. This can further ease the manipulation and implantation of the cuff electrode assembly 116a.

Figure 3C:
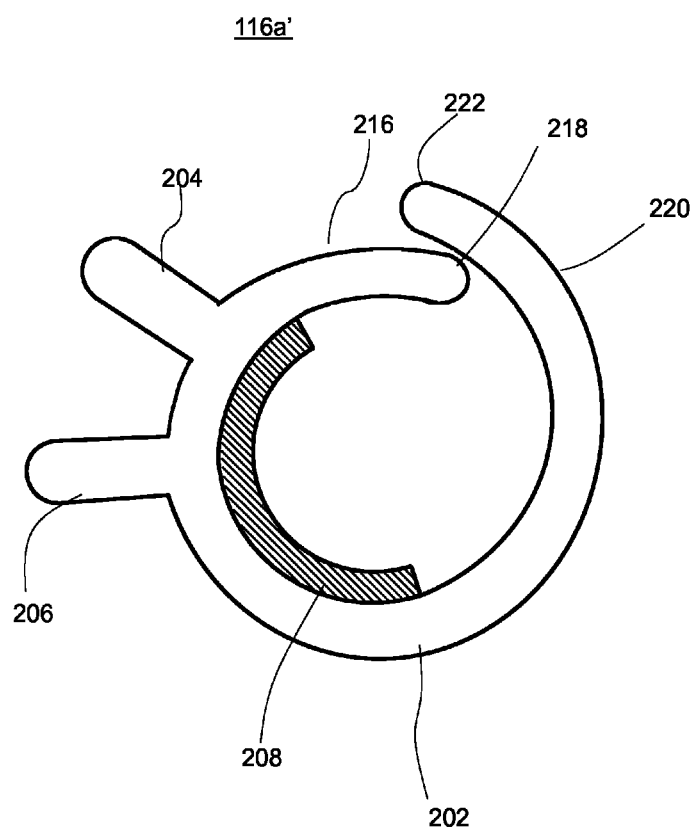
FIG. 3C is a schematic front view of an alternative cuff electrode assembly in a closed configuration that can be used in relation to embodiments of the present invention.

FIG. 3C is a front view of an alternative cuff electrode assembly 116a' in a closed configuration according to one embodiment. As shown in FIG. 3C, the cuff electrode assembly 116a' can be of substantially the same construction as the cuff electrode assembly 116a described herein. In the illustrated embodiment, the cuff electrode assembly 116a' differs from the cuff electrode assembly 116a in that in the closed configuration of the cuff body 202, the second end portion 220 overlaps the first end portion 216, such that the second free end 222 is positioned adjacent to and radially outward of the first free end 218. Thus, as shown in FIG. 3C, the cuff electrode assembly 116a' can have the capability to encircle the target nerve upon which it is placed by greater than 360 degrees.

Figure 4:
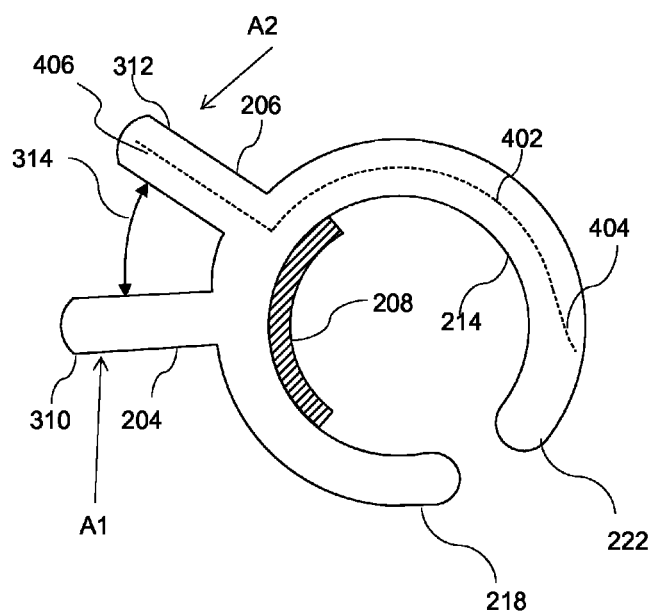
FIG. 4 is a schematic front view of the cuff electrode assembly in an alternative embodiment with a stiffening member.

FIG. 4 shows a schematic perspective view of an alternative embodiment of the cuff electrode assembly 116a (as illustrated in FIGS. 1 and 2), including a stiffening member 402 incorporated into the polymeric cuff body 202. In an embodiment, the stiffening member 402 is embedded within the flexible insulating polymer of the cuff body 116a. The stiffening member 402 has a first end portion 404 and an opposite second end portion 406. The first end portion 404 can be disposed proximate to the second arm member 206, and the second end portion 406 can be disposed proximate to the second free end 218 of the cuff body 116a. In the illustrated embodiment, the stiffening member 402 is in the form of a ribbon of material embedded in the polymeric material forming the remainder of the cuff body 202. In various embodiments, the stiffening member 402 can be made of a polymeric or metallic material sized and shaped to provide a desired degree of stiffness and resiliency to the cuff body 202. In various embodiments, the stiffening member 402 is preformed so as to cause the cuff body 202 to close upon removal of the externally applied force, urging the first and second end arm members 204 and 206 toward one another as discussed previously. In such embodiments, the stiffening member 402 can be configured to maintain the cuff body 202 in the closed configuration, substantially surrounding the target nerve 102 (illustrated in FIGS. 1 and 2) upon removal of the force such that the first end portion 218 and the second end portion 222 of the cuff body 202 can encircle the target nerve 102 to form a C shape or split cylinder type shape.

In an embodiment, the stiffening member 402 can be provided within the flexible, insulating polymer of the cuff body 202. In an embodiment, the stiffening member 402 can be placed along the inner surface 214 of the cuff body 202. In an embodiment, the stiffening member 402 can be formed of a reinforcing material and/or a shape memory alloy member embedded in the flexible, electrically insulating polymer of the cuff body 202. The reinforcing material can be configured to maintain stable shape and provide retention of the shape of the cuff body 202, i.e., shape of the cuff body 202 during the open configuration and the closed configuration. The stiffening member 402 can be made of an elastic material that is capable of regaining its shape substantially upon removal of the applied force.

In various embodiments, the stiffening member 402 can be a metallic, electrically conductive element that also operates as the electrode for the cuff electrode assembly 116a. In such embodiments, an inner surface of the stiffening member 402 can be exposed so as to be capable of contact with the target nerve 102 when the cuff electrode assembly 116a is placed thereupon. Additionally, in such embodiments, the stiffening member 402 is electrically coupled to the conductor element of the conductor member 115 (see FIGS. 1 and 2).

Figure 5A:
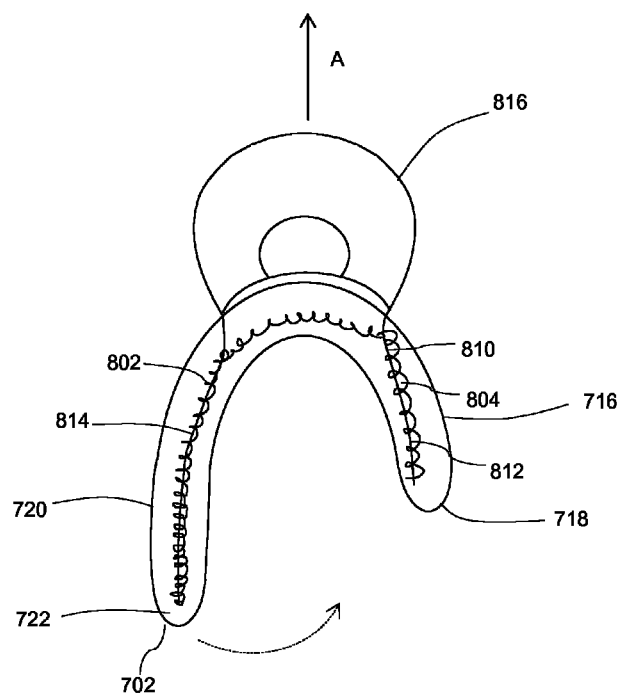
FIGS. 5A and 5B are schematic front views of the cuff electrode assembly showing a stiffening pin that can be used in relation to embodiments of the present invention.

FIG. 5A is a schematic front view of an alternative embodiment of a cuff electrode assembly 616a in an open configuration for placement on a target nerve. In the illustrated embodiment, the cuff electrode assembly 116 includes a cuff body 702 having a first end portion 716 with a first free end 718, a second end portion 720 having a second free end 722, and a stiffening member 802. As shown, the stiffening member 802 is in the form of a helical coil extending within the cuff body 702 defining a lumen 804. As will be appreciated, the cuff electrode assembly 616a also includes at least one electrode similar or identical to the electrode 208 of the cuff electrode assemblies described herein.

Figure 5B:
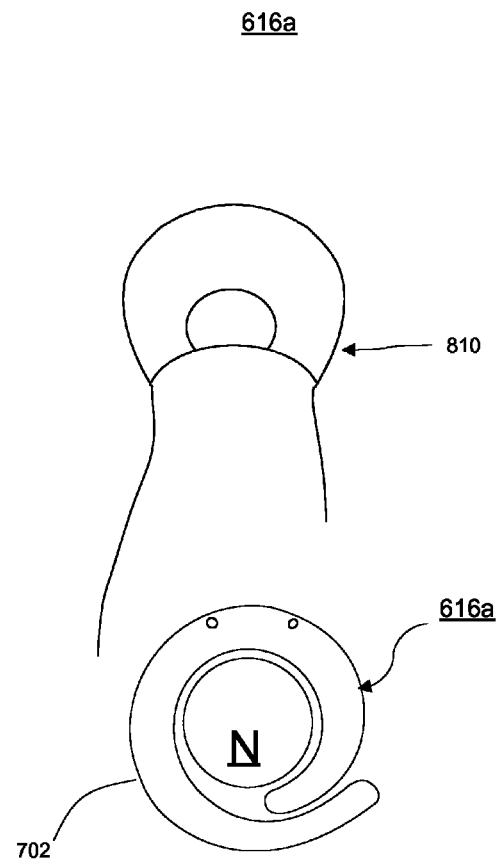

As further shown, a stiffening pin 810 is provided having a first portion 812, an opposite second portion 814, and a handle portion 816. As shown, the first and second portions 812, 814 are positioned within the lumen 804 within, respectively, the first end portion 716 and the second end portion 720 of the cuff body 702. When positioned as shown in FIG. 5, the stiffening pin 810 operates to maintain the cuff body 702 in the open configuration for placement about the target nerve. As indicated by the arrow A in FIG. 5A, the stiffening pin 810 is removable from the cuff body 702, thus allowing the cuff body 702 to assume its closed, implanted position on the target nerve N as shown in FIG. 5B. As can be seen in FIG. 5A, the stiffening pin 810 can positioned asymmetrically with respect to the free ends 718, 722 of the cuff body 702, such that the first end portion 716 has a relatively short length compared to the second end portion 720. This configuration results in a relatively short length of the cuff body 702 that must be wrapped around the side of the target nerve opposite the clinician, as described previously herein.

In an embodiment, the stiffening member 802 can be configured to enhance the relative stiffness of the cuff body 702, and can operate to bias the cuff body 702 toward its closed configuration. The stiffening member 802 and the stiffening pin 810 can be made of any variety of metal or polymeric materials, including those described in connection with the stiffening member 402 described previously.

Figure 6:
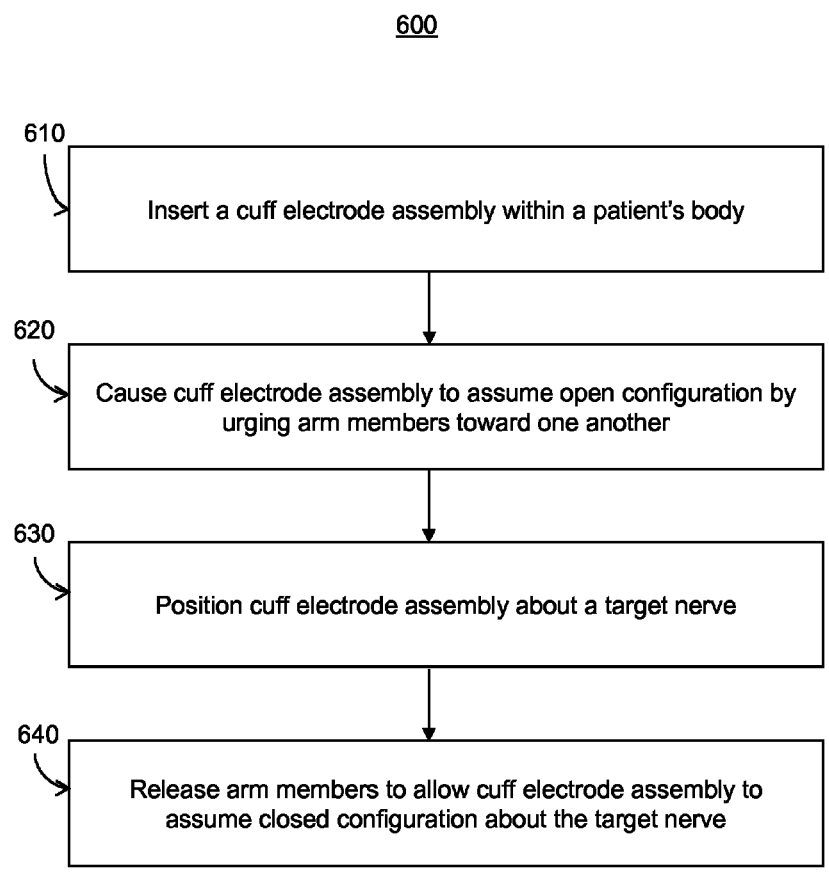
FIG. 6 is a flow chart illustrating a method for implanting a cuff electrode assembly on a target nerve.

FIG. 6 is a flow chart illustrating a method 600 for implanting a nerve cuff electrode assembly similar to the cuff electrode assembly 116a (116b or 116c) on a target nerve 102. The method 600 includes inserting the cuff electrode assembly 116a within a patient's body at step 610. In an embodiment, the cuff electrode assembly 116a is inserted to a location on or proximate to the target nerve 102 (shown in FIGS. 1 and 2) such as the right vagus nerve.

The method 600 further includes, at step 620, applying force to at least one of the first and second arm members 204 and 206, so as to urge the arm members 204, 206 toward one another thereby causing the first and second free ends 218 and 222 to deflect away from one another such that the cuff body 202 assumes the open configuration. The method 600 further includes placing the cuff electrode assembly 116a about the target nerve 102 such that the cuff body 202 can at least partially surround the target nerve 102 at step 630. The method 600 further includes, at step 640, releasing the force to cause or allow the cuff body 202 to return to its closed configuration and thereby wrap around the target nerve 102. Upon assuming its closed configuration, the cuff electrode assembly 116a can apply a radial force on the target nerve 102 to secure the cuff electrode assembly 116a in place.

In an alternative method, the cuff electrode assembly 616a can be implanted. According to this embodiment, with the stiffening pin 810 positioned in the lumen 804 as shown in FIG. 5A, thus maintaining the cuff body 702 in the open configuration, the method includes positioning the cuff electrode assembly 616a partially about the target nerve. When positioned as desired, the clinician can then remove the stiffening pin 810 while holding the cuff body 702 in place. Upon removal of the stiffening pin 810, the cuff body 702 will tend to resume its closed configuration and wrap at least partially around the target nerve N (shown in FIG. 5B). The foregoing steps can be repeated for each additional cuff electrode assembly 616a, if any, on the lead assembly being implanted.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

What is claimed is:

1. A cuff electrode assembly for implantation on a target nerve, the cuff electrode assembly comprising:
a resilient cuff body configured to be disposed about the target nerve, the cuff body including a proximal end, a distal end, a first end portion having a first free end, and a second end portion having a second free end, the first free end and the second free end defining a gap in the cuff body between the first free end and the second free end, wherein the cuff body is pre-formed to assume a closed configuration having a generally annular cross-sectional shape, the gap extending straight along a longitudinal axis of the cuff body from the distal end of the cuff body to the proximal end of the cuff body;
a first arm member and a second arm member each projecting radially outward from the cuff body and spaced from one another along the cuff body, wherein each of the first and second arm members is disposed closer, as measured circumferentially around the cuff body in a first direction as compared to a second direction opposite the first direction, to the gap in the cuff body, and further wherein the cuff body is configured such that a force applied to urge the first and second arm members toward one another causes relative deflection of the second free end and the first free end away from one another to expand the gap and define an open configuration of the cuff body configured to allow the cuff body to be positioned around the target nerve; and
an electrode disposed at least partially within or on the cuff body oriented to provide an electrical stimuli to the target nerve when the cuff body is disposed about the target nerve.

2. The cuff electrode assembly of claim 1, wherein a length of the cuff extending from the first free end to the second free end spans an angle less than 360 degrees.

3. The cuff electrode assembly of claim 1, wherein the cuff body is pre-formed such that in the closed configuration the first free end and the second free end are spaced apart from one another without overlap so such that the cuff body further defines a generally circular cross-sectional.

4. The cuff electrode assembly of claim 1, wherein the first arm member is positioned closer than the second arm member to the first free end, and wherein the second arm member is positioned along the cuff body between the first arm member and the second free end.

5. The cuff electrode assembly of claim 1, wherein the cuff body is configured such that the first arm member remains relatively stationary and the second arm member deflects toward the first arm member upon application of a force to the second arm member in the direction of the first arm member so as to cause the cuff body to assume the open configuration.

6. The cuff electrode assembly of claim 1, wherein the cuff body is configured such that a length of the first end portion between the first arm member and the first free end remains relatively stationary upon application of a force to the second arm member urging the second arm member toward the first arm member.

7. The cuff electrode assembly of claim 1, wherein the cuff body is made substantially of a flexible, electrically insulating polymer.

8. The cuff electrode assembly of claim 7, wherein the flexible insulating polymer is silicone rubber.

9. The cuff electrode assembly of claim 7, wherein the cuff body further includes a reinforcing material in the flexible, electrically insulating polymer.

10. The cuff electrode assembly of claim 7, wherein the cuff body further includes a stiffening member within the flexible, insulating polymer.

11. The cuff electrode assembly of claim 1, further comprising a stiffening member configured to urge the cuff body to return to the pre-formed shape upon release of a force causing the cuff body to assume the open configuration.

12. The cuff electrode assembly of claim 11, wherein the stiffening member is embedded within a flexible insulating polymer and has a first end portion and an opposite second end portion, the first end portion disposed proximate the second arm member, and the second end portion disposed proximate the second free end of the cuff body.

13. The cuff electrode assembly of claim 1, wherein in the closed configuration the second end portion of the cuff body overlaps the first end portion of the cuff body.

14. A lead assembly configured for stimulating a target nerve, the lead assembly comprising:
at least one cuff electrode assembly configured for implantation about the target nerve, the cuff electrode assembly comprising:
a resilient cuff body configured to be disposed about the target nerve, the cuff body including a proximal end, a distal end, a first end portion having a first free end, and a second end portion having a second free end, the first free end and the second free end defining a gap in the cuff body between the first free end and the second free end, wherein the cuff body is pre-formed to assume a closed configuration having a generally annular cross-sectional shape, the gap extending straight along a longitudinal axis of the cuff body from the distal end of the cuff body to the proximal end of the cuff body;
a first arm member and a second arm member each projecting radially outward from the cuff body and spaced from one another along the cuff body, wherein each of the first and second arm members is disposed closer, as measured circumferentially around the cuff body in a first direction as compared to a second direction opposite the first direction, to the gap in the cuff body and further wherein the cuff body is configured such that a force applied to urge the first and second arm members toward one another causes relative deflection of the second free end and the first free end away from one another to expand the gap and define an open configuration of the cuff body configured to allow the cuff body to be positioned around the target nerve;
an electrode disposed at least partially within or on the cuff body oriented to provide an electrical stimuli to the target nerve when the cuff body is disposed about the target nerve;
a flexible lead body made of an insulating material, the lead body having a proximal end portion and a distal end portion;
an insulated flexible conductor member at least partially disposed within the lead body, the conductor member including a distal end electrically and mechanically coupled to the electrode of the cuff electrode assembly; and
a connector assembly coupled to the proximal end portion of the lead body and to the conductor member, the connector assembly configured to electrically couple the conductor member to an implantable stimulator.

15. The lead assembly of claim 14, wherein the at least one cuff electrode assembly includes a plurality of cuff electrode assemblies, and wherein the lead further includes a plurality of insulated, flexible conductor members at least partially disposed within the lead body, and wherein an electrode of each of the plurality of cuff electrode assemblies is electrically and mechanically coupled to one of the plurality of conductor members.

16. The lead assembly of claim 14, wherein the cuff electrode assembly further comprises a stiffening member configured to urge the cuff body to return to the pre-formed shape upon release of a force causing the cuff body to assume the open configuration.

17. The lead assembly of claim 14, wherein in the closed configuration the second end portion of the cuff body overlaps the first end portion of the cuff body.

18. A method for implanting a cuff electrode assembly on a target nerve, the method comprising:
inserting an implantable cuff electrode assembly within a patient's body, the cuff electrode assembly including:
a resilient cuff body configured to be disposed about the target nerve, the cuff body including a proximal end, a distal end, a first end portion having a first free end, and a second end portion having a second free end, the first free end and the second free end defining a gap in the cuff body between the first free end and the second free end, wherein the cuff body is pre-formed to assume a closed configuration having a generally annular cross-sectional shape, the gap extending straight along a longitudinal axis of the cuff body from the distal end of the cuff body to the proximal end of the cuff body;
a first arm member and a second arm member each projecting radially outward from the cuff body and spaced from one another along the cuff body, wherein each of the first and second arm members is disposed closer, as measured circumferentially around the cuff body in a first direction as compared to a second direction opposite the first direction, to the gap in the cuff body, and further wherein the cuff body is configured such that a force applied to urge the first and second arm members toward one another causes relative deflection of the second free end and the first free end away from one another to expand the gap and define an open configuration of the cuff body configured to allow the cuff body to be positioned around the target nerve; and
an electrode disposed at least partially within or on the cuff body oriented to provide an electrical stimuli to the target nerve when the cuff body is disposed about the target nerve;
applying a force to at least one of the first and second arm members to urge the first and second arm members toward one another thereby causing the first and second free ends to deflect away from one another such that the cuff body widens the gap to assume the open configuration;
with the cuff body in the open configuration, placing the cuff electrode assembly proximate the target nerve such that the cuff body at least partially surrounds the target nerve; and
releasing the force urging the first and second arm members together to narrow the gap.

19. The method of claim 18, wherein the cuff electrode assembly is a first cuff electrode assembly of an implantable lead assembly including one or more additional cuff electrode assemblies, the one or more additional cuff electrode assemblies being coupled to the first cuff electrode assembly.

20. The method of claim 19, wherein the method further comprises simultaneously opening the first cuff electrode assembly and the one or more additional cuff electrode assemblies.

* * * * *